US00PP24837P2

(12) United States Plant Patent
Barbour et al.

(10) Patent No.: US PP24,837 P2
(45) Date of Patent: Sep. 2, 2014

(54) OAK TREE NAMED 'GREENENVY'

(50) Latin Name: *Quercus phellos*
Varietal Denomination: Greenenvy

(75) Inventors: John Hinds Barbour, Hawkinsville, GA (US); Sam Rogers, Bonaire, GA (US)

(73) Assignee: Athena Trees, Inc., Hawkinsville, GA (US)

( * ) Notice: Subject to any disclaimer, the term of this patent is extended or adjusted under 35 U.S.C. 154(b) by 16 days.

(21) Appl. No.: 13/507,452

(22) Filed: Jun. 30, 2012

(51) Int. Cl.
*A01H 5/00* (2006.01)

(52) U.S. Cl.
USPC ..... Plt./225

(58) Field of Classification Search
USPC ..... Plt./225
See application file for complete search history.

*Primary Examiner* — Annette Para
(74) *Attorney, Agent, or Firm* — C. A. Whealy

(57) ABSTRACT

A new and distinct cultivar of Oak tree named 'Greenenvy', characterized by its upwardly sweeping lateral branches forming a dense and narrow pyramidal plant form; vigorous growth habit; and relatively large, dark green-colored and glossy leaves.

8 Drawing Sheets

Botanical designation: *Quercus phellos.*
Cultivar denomination: 'GREENENVY'.

BACKGROUND OF THE INVENTION

The present invention relates to a new and distinct cultivar of Oak tree, botanically known as *Quercus phellos*, commercially referred to as Willow Oak and hereinafter referred to by the name 'Greenenvy'.

The new Oak tree originated from an open-pollination in Walton County, Ga. of an unnamed selection of *Quercus phellos*, not patented, as the female, or seed, parent with an unknown selection of *Quercus phellos* as the male, or pollen, parent. The new Oak tree was discovered and selected by the Inventors as a single plant from within the progeny of the stated open-pollination in a controlled greenhouse environment in Walton County, Ga. in 2000.

Asexual reproduction of the new Oak tree by softwood cuttings in a controlled environment in Oconee County, Ga. since 2007 has shown that the unique features of this new Oak tree are stable and reproduced true to type in successive generations.

SUMMARY OF THE INVENTION

Trees of the new Oak have not been observed under all possible environmental and cultural conditions. The phenotype may vary somewhat with variations in environmental conditions such as temperature and light intensity without, however, any variance in genotype.

The following traits have been repeatedly observed and are determined to be the unique characteristics of 'Greenenvy'. These characteristics in combination distinguish 'Greenenvy' as a new and distinct Oak tree:

1. Upwardly sweeping lateral branches forming a dense and narrow pyramidal plant form.
2. Vigorous growth habit.
3. Relatively large, dark green-colored and glossy leaves.

Trees of the new Oak can be compared to plants of the female parent selection. Trees of the new Oak differ primarily from trees of the female parent selection in branch orientation as trees of the new Oak have more upwardly sweeping lateral branches than trees of the female parent selection. In addition, trees of the new Oak have larger leaves than trees of the female parent selection.

Trees of the new Oak can also be compared to plants of *Quercus phellos* 'QPSTA', disclosed in U.S. Plant Pat. No. 13,677. Trees of the new Oak and 'QPSTA' differ primarily in branch orientation and plant form as trees of the new Oak have more upwardly sweeping lateral branches whereas trees of 'QPSTA' have more laterally-orientated lateral branches. In addition, trees of the new Oak have larger leaves than trees of 'QPSTA'.

BRIEF DESCRIPTION OF THE PHOTOGRAPHS

The accompanying colored photographs illustrate the overall appearance of the new Oak tree showing the colors as true as it is reasonably possible to obtain in colored reproductions of this type. Colors in the photographs may differ slightly from the color values cited in the detailed botanical description which accurately describe the colors of the new Oak tree.

The photographs on the first sheet comprise side perspective views of typical trees of 'Greenenvy' and 'QPSTA' grown during the winter in outdoor environments showing the differences in branch orientation and plant form.

The photograph on the second sheet comprises a side perspective view of a typical tree of 'Greenenvy' grown during the spring in an outdoor nursery.

The photograph on the third sheet is a close-up view of the upper surface of typical leaves of 'Greenenvy' grown during the spring.

The photograph on the fourth sheet is a close-up view of the lower surface of typical leaves of 'Greenenvy' grown during the spring.

The photograph on the fifth sheet is a close-up view of the upper surfaces of typical leaves of 'QPSTA' (left) and 'Greenenvy' (right) grown during the summer.

The photograph on the sixth sheet is a close-up view of the upper surfaces of typical leaves of 'QPSTA' (left) and 'Greenenvy' (right) grown during the summer.

The photograph on the seventh sheet is a close-up view of typical acorns of 'Greenenvy'.

The photograph on the eighth sheet is a close-up view of a section of trunk of a typical tree of 'Greenenvy' grown in an outdoor nursery.

DETAILED BOTANICAL DESCRIPTION

The aforementioned photographs and following observations, measurements and values describe plants grown in an outdoor nursery in Pulaski County, Ga. and under cultural practices typical of Oak tree commercial production. Trees were five years old when the photographs and description were taken. In the following description, color references are made to The Royal Horticultural Society Colour Chart, 2007 Edition, except where general terms of ordinary dictionary significance are used.

Botanical classification: *Quercus phellos* 'Greenenvy'.

Parentage:

*Female, or seed, parent*.—Unnamed selection of *Quercus phellos*, not patented.

*Male, or pollen, parent*.—Unknown selection of *Quercus phellos*, not patented.

Propagation:

*Type*.—By softwood cuttings.

*Root description*.—Fibrous.

*Time to rooting*.—About three to four weeks.

Plant description:

*Plant form and growth habit*.—Upright tree with upwardly sweeping lateral branches forming a dense and narrow pyramidal plant form; freely branching habit with numerous lateral branches developing per plant; vigorous growth habit.

*Plant height*.—About 10.36 meters.

*Plant diameter*.—About 5.79 meters.

*Height to width ratio*.—About 1.8.

*Branch orientation*.—Lower canopy branches, about 50.76° from central leader; upper canopy branches, about 34.4° from central leader.

*Lateral branch color*.—Close to 166A.

*Trunk diameter, about* 30.5 *cm above ground level*.—About 33 cm.

*Immature bark*.—Texture: Smooth, glabrous. Color: Close to 198A mottled with close to 202D.

*Mature bark*.—Texture: Rough with irregular furrows and thick and scaly ridges. Color: Close to 202B mottled with close to N200C.

*Leaf arrangement*.—Alternate, simple.

*Leaf length*.—About 13.46 cm.

*Leaf width*.—About 2.86 cm.

*Leaf shape*.—Narrowly elliptical or lanceolate; margins, entire and slightly undulate; apex, acute to obtuse; base, cuneate with obtuse tendencies; venation, pinnate.

*Leaf texture, upper and lower surfaces*.—Smooth, glabrous.

*Leaf luster, upper and lower surfaces*.—Glossy.

*Leaf color, summer*.—Upper surface: Close to 137B. Lower surface: Close to 146B.

*Leaf color, autumn*.—Upper and lower surfaces: Close to 13A.

*Leaf petioles*.—Length: About 6.35 cm to 9.53 cm. Diameter: About 4.23 mm. Texture, upper and lower surfaces: Smooth, glabrous. Color, upper and lower surfaces: Close to 146B.

*Leaf buds*.—Length: About 3.18 cm to 6.35 cm. Texture: Pubescent; margins, ciliate. Color: Close to 177A.

Flower description:

*Flower arrangement and habit*.—Flowers are of the new Oak tree are similar to flowers of other varieties and selections of *Quercus phellos*. Flowers monoecious; staminate flowers arranged in clustered pendent catkins, calyx, four to seven-lobed with at least six stamens; pistillate flowers are solitary or arranged in axillary spikes, calyx, six-lobed.

*Fragrance*.—None detected.

*Natural flowering season*.—Trees of the new Oak begin flowering in early April in Pulaski County, Ga.

*Flower longevity*.—Individual flowers last about ten days to two weeks on the plant; flowers not persistent.

*Acorns*.—Size: About 1.27 cm by 1.27 cm. Color: Close to 165A and 199D.

Winter hardiness: Trees of the new Oak have been observed to be hardy to USDA Hardiness Zone 8a.

Pathogen & pest resistance: Trees of the new Oak have been not observed to be resistant to pathogens and pests common to Oak trees.

It is claimed:

1. A new and distinct Oak tree named 'Greenenvy' as illustrated and described.

* * * * *

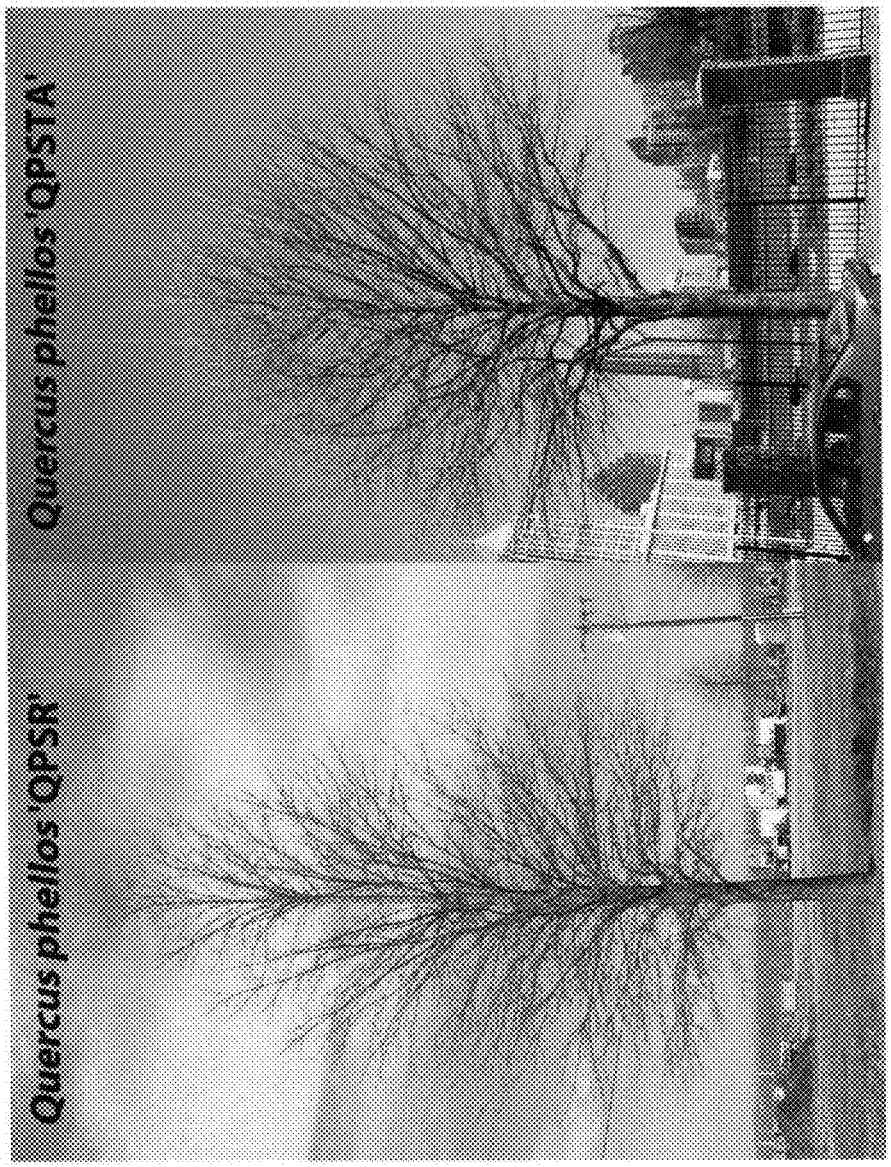
Quercus phellos 'QPSR'
Quercus phellos 'QPSTA'

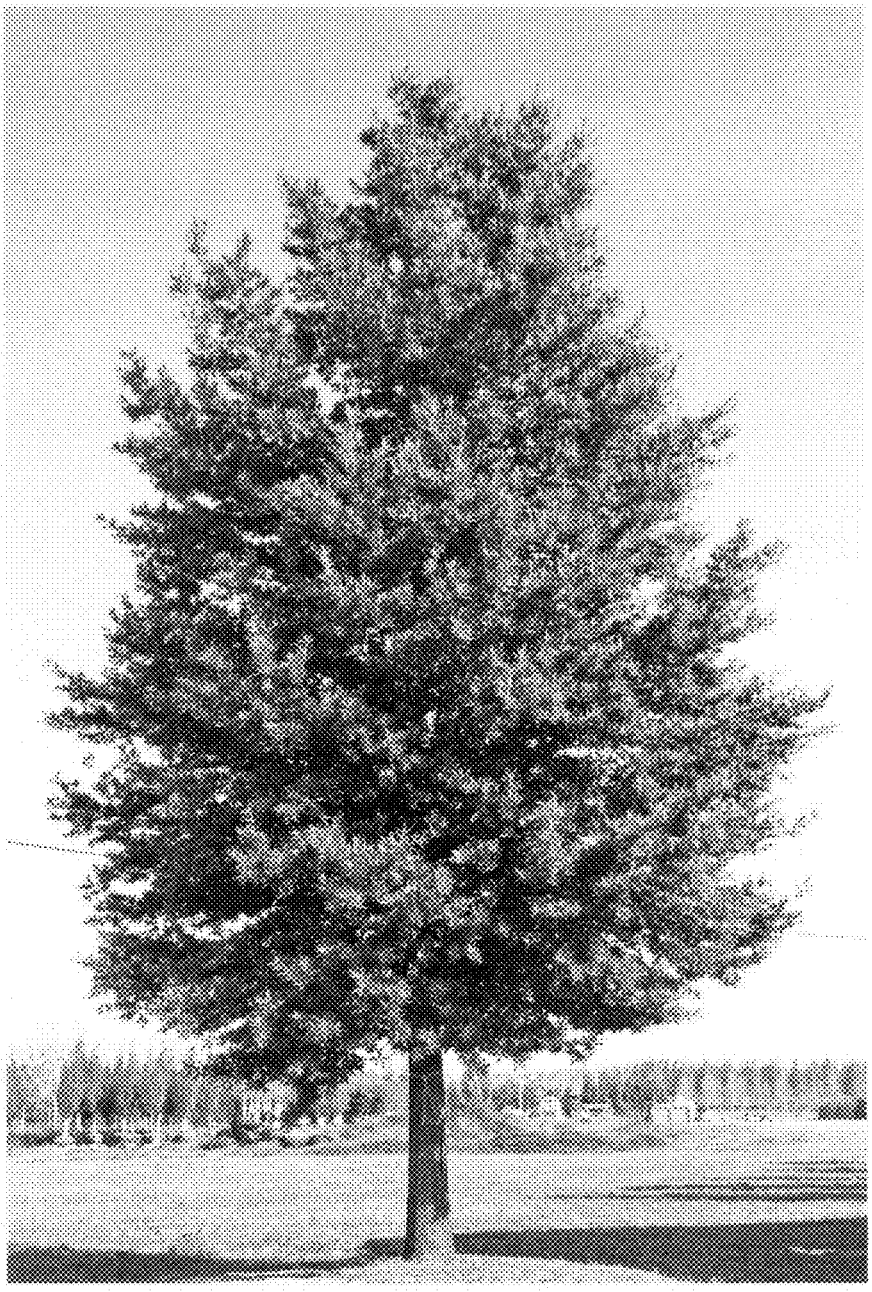

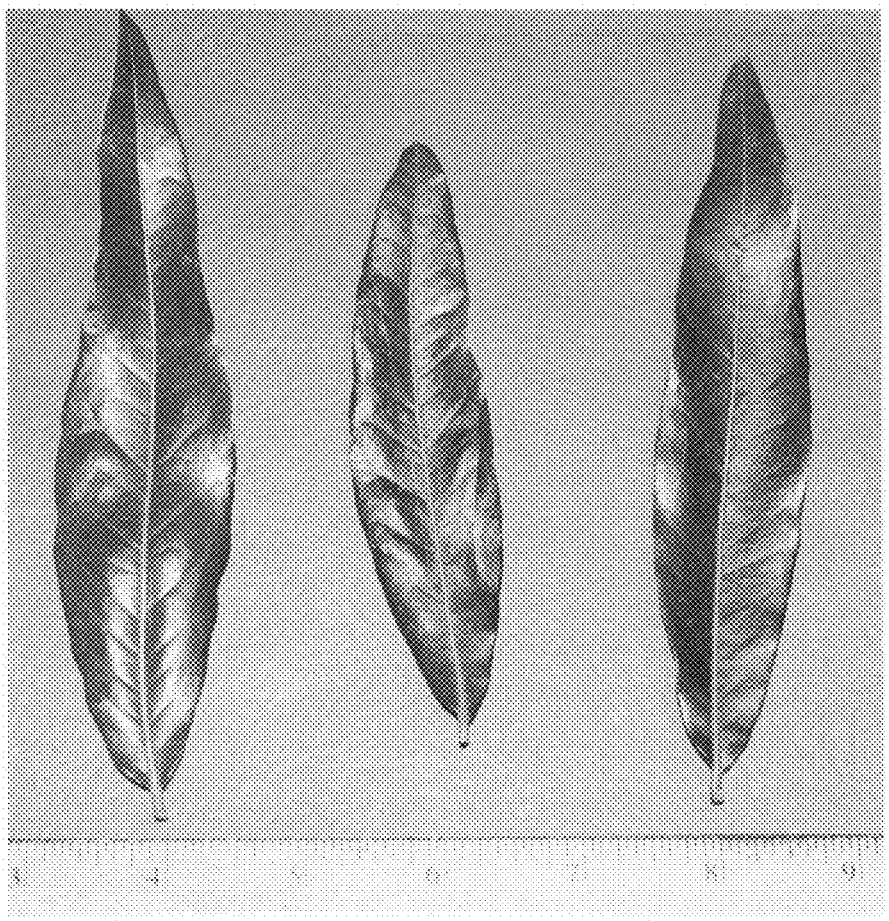

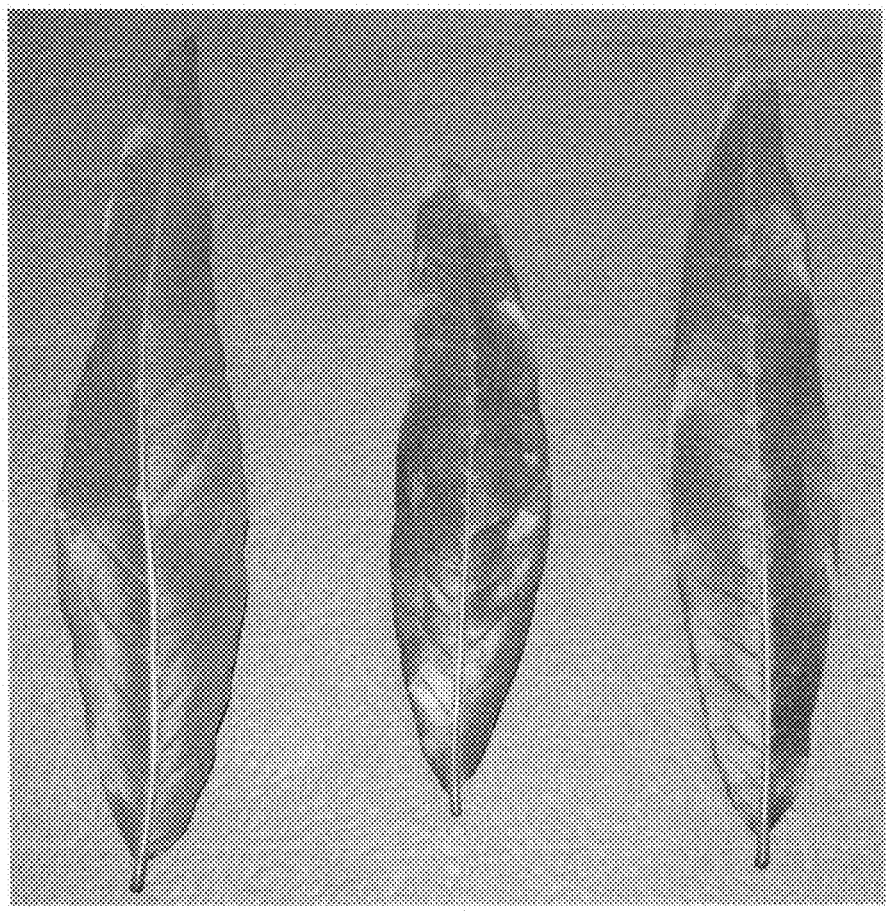

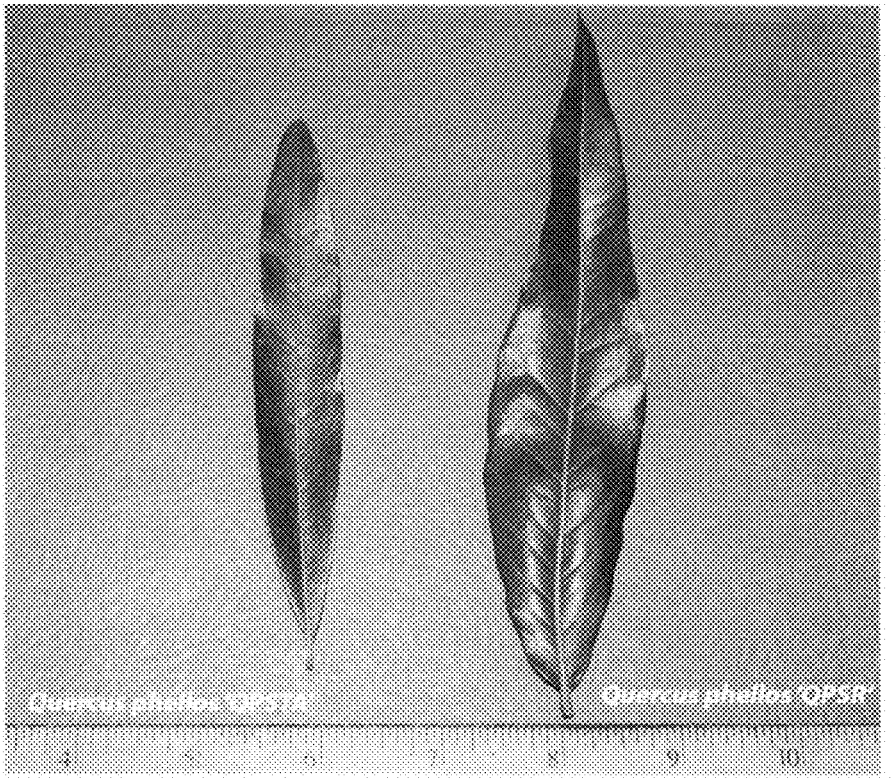
Quercus phellos 'QPSR'
Quercus phellos 'QPSR'

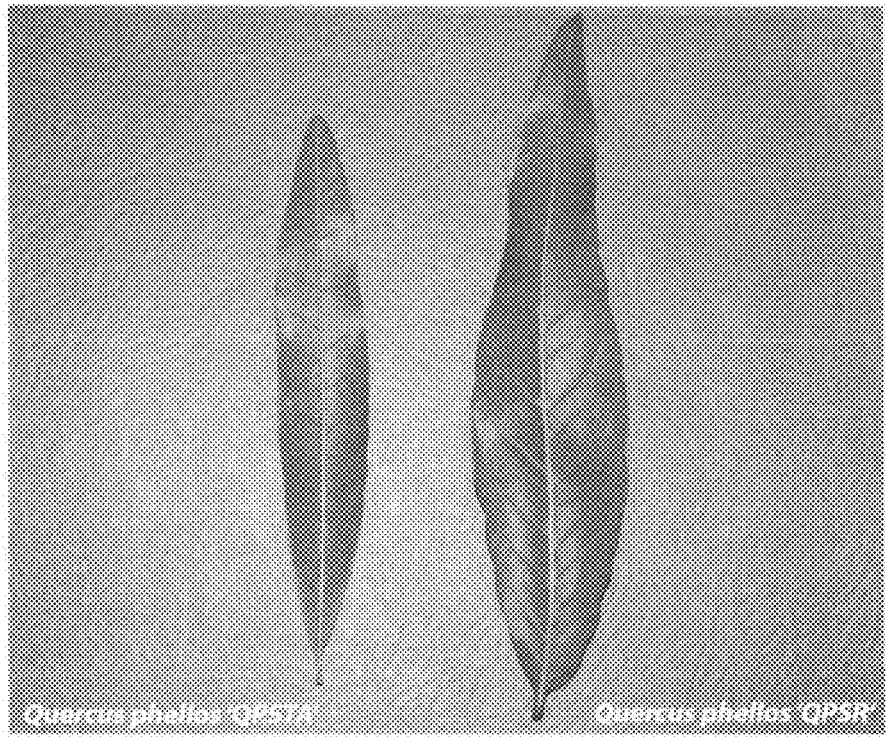
Quercus phellos 'QPS7R'
Quercus phellos 'QPS7R'

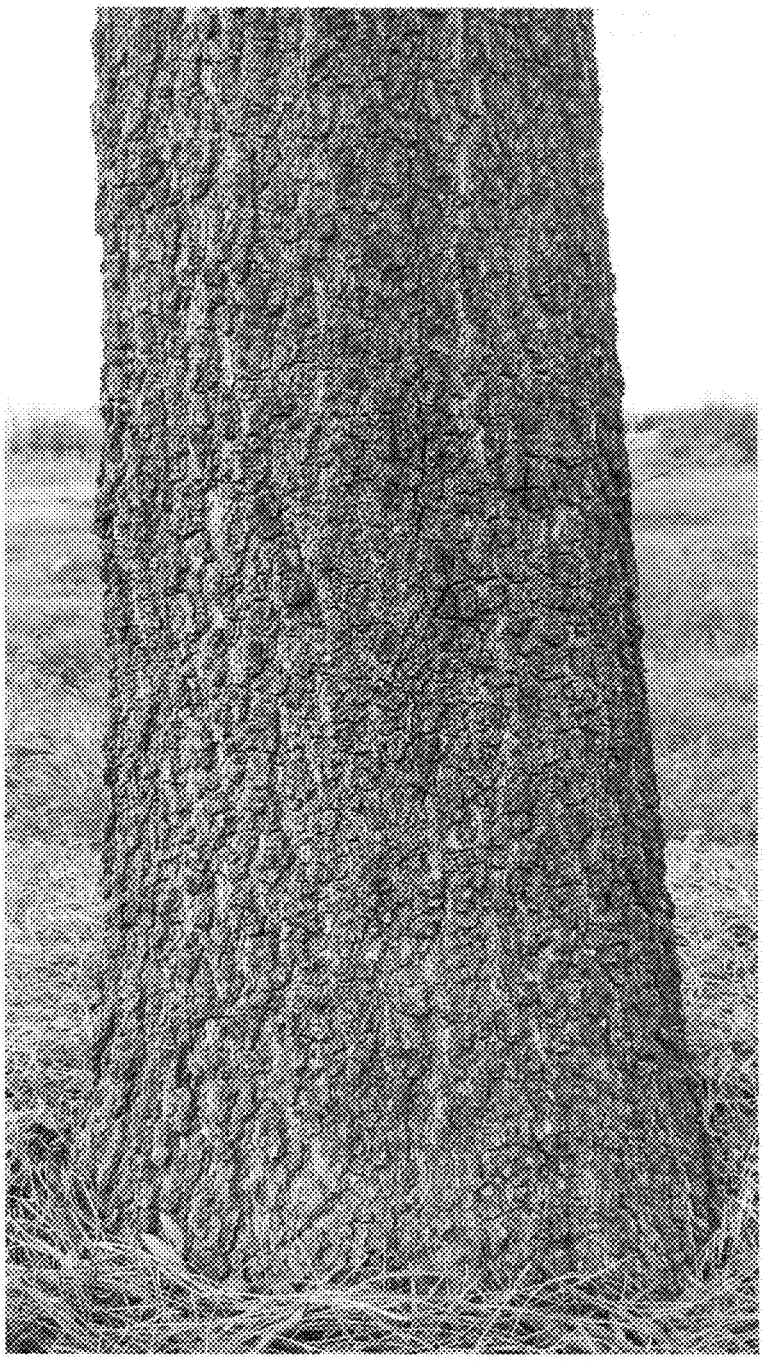

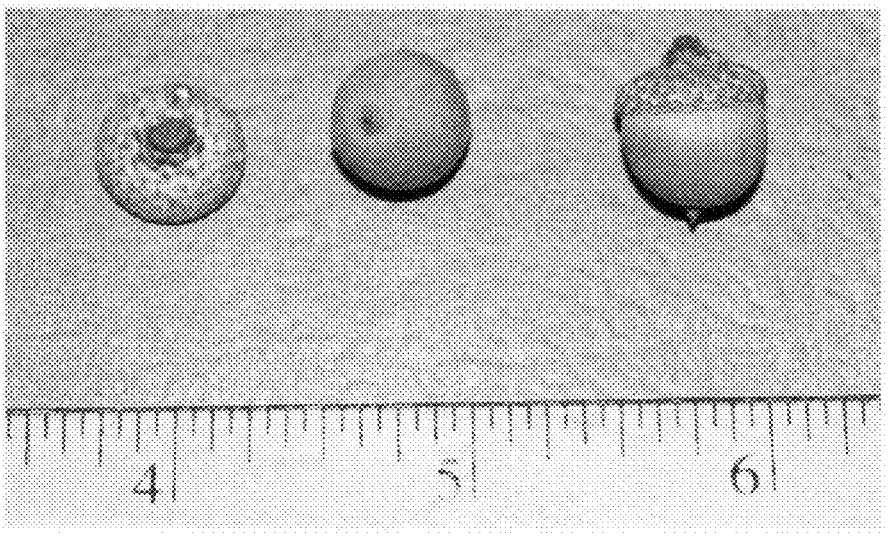
4
5
6